(12) United States Patent
Dixon (10) Patent No.: US 8,529,942 B2
(45) Date of Patent: Sep. 10, 2013

(54) WOUND CARE DRESSING

(76) Inventor: David M. Dixon, Tucson, AZ (US)

( * ) Notice: Subject to any disclaimer, the term of this patent is extended or adjusted under 35 U.S.C. 154(b) by 0 days.

(21) Appl. No.: 13/073,858

(22) Filed: Mar. 28, 2011

(65) Prior Publication Data

US 2011/0172580 A1 Jul. 14, 2011

Related U.S. Application Data

(62) Division of application No. 11/231,022, filed on Sep. 19, 2005, now Pat. No. 7,914,812.

(60) Provisional application No. 60/611,184, filed on Sep. 17, 2004.

(51) Int. Cl.
*A61F 13/00* (2006.01)
*A61L 15/00* (2006.01)
*A61F 13/20* (2006.01)

(52) U.S. Cl.
USPC ........................... 424/443; 424/445; 604/383

(58) Field of Classification Search
None
See application file for complete search history.

(56) References Cited

U.S. PATENT DOCUMENTS

| 618,428 A | 1/1899 | Morrison et al. |
|---|---|---|
| 4,401,651 A | 8/1983 | Knutson |
| 2003/0003135 A1 | 1/2003 | Leung et al. |
| 2004/0005350 A1 | 1/2004 | Looney et al. |
| 2004/0122396 A1 | 6/2004 | Maldonado et al. |

FOREIGN PATENT DOCUMENTS

WO WO9613282 9/1996

OTHER PUBLICATIONS

Canadian Office Action dated May 28, 2012.

*Primary Examiner* — Robert A Wax
*Assistant Examiner* — Jeffrey T Palenik
(74) *Attorney, Agent, or Firm* — Dale F. Regelman; Quarles & Brady LLP (57) ABSTRACT

A wound care dressing comprising one or more nonwoven blankets, where each nonwoven blanket comprises a plurality of fibers, where each of the plurality of fibers are formed from one or more saccharides in optional combination with one or more medicaments.

14 Claims, 6 Drawing Sheets

WOUND CARE DRESSING

CROSS REFERENCE TO RELATED APPLICATIONS

This application is a Divisional Application which claims priority from a U.S. Non-Provisional Application having Ser. No. 11/231,022, filed Sep. 19, 2005, now U.S. Pat. No. 7,914,812, which claimed priority from a U.S. Provisional Application having Ser. No. 60/611,184 filed Sep. 17, 2004.

FIELD OF THE INVENTION

The invention is directed to a wound care dressing and method using that wound care dressing to treat wounds.

BACKGROUND OF THE INVENTION

It is known in the art to treat wounds with one or more sugars. U.S. Pat. No. 4,401,651 teaches a method to treat wounds using a paste formed from sucrose and one or more carriers. Such carriers included agar, cold cream, corn oil, cottonseed oil, gelatin, glycerin, lanolin, olive oil, peanut oil, polyethylene glycol, and the like.

The '651 patent teaches that it not practicable to adhere the saccharide paste compositions to a dressing. Rather, the paste compositions of the '651 patent must be manually prepared and then manually spread directly onto and/or into the wounds.

What is needed is a more convenient composition and method to apply one or more saccharides, in combination with one or more medicaments, to a wound to facilitate rapid healing.

SUMMARY OF THE INVENTION

Applicant's invention comprises a wound care dressing comprising one or more nonwoven blankets, where those one or more nonwoven blankets are each formed from a saccharide in optional combination with one or more medicaments.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

This invention is described in preferred embodiments in the following description with reference to the Figures, in which like numbers represent the same or similar elements.

Applicant's wound care dressing is engineered to facilitate the healing of a wound as well as provide a barrier to microorganisms. Applicant's wound care dressing also assists with infection control by providing a broad range of one or more antifungal, one or more antibacterial, one or more antiviral, and/or one or more antiprotozonal medicaments directly to the wound, bypassing the gut and blood stream. Applicant's wound care dressing also facilitates debridement while expediting the healing process by encouraging a moist, germ free environment. In certain embodiments, Applicant's wound care dressing further comprises a pulsitile delivery system for one or more medicaments, wherein in certain embodiments those one or more medicaments are administered sequentially to external surfaces of, for example and without limitation, the skin, bones, cartilage, and organs, and wherein in certain embodiments those one or more medicaments are released sequentially internally, e.g. to the internal surface of a blood vessel.

In certain embodiments, Applicant's medicaments comprise, without limitation: anti-bacterials, anti-virals, anti-fungals, anti-protozoals, anti-coagulants, additional saccharides and polyols, coral, beta-blockers, anti-spasmodics, etc, and any substance that is able to be utilized and/or absorbed by cells at the surface for use at a local site of application or systemically. The various medicaments selected may have a local, systemic or a combination of the two side effects (e.g. healing, coagulation, muscle relaxing, etc.)

As those skilled in the art will appreciate, Human Immunodeficiency Virus, or HIV, is the virus that causes acquired immune deficiency syndrome (AIDS). The virus weakens a person's ability to fight infections and cancer. Patients with HIV are said to have AIDS when they develop certain infections or skin cancers or when their CD4 count is less than 200.

HIV attacks and destroys a type of white blood cell called a CD4 cell. This cell's main function is to fight disease. When a person's CD4 cell count gets low, they are more susceptible to illnesses and skin infections. Patients afflicted with AIDS are extremely vulnerable to various infections, called AIDS defining illnesses, and often exhibit the following conditions: [0022] Kaposi's sarcoma, a skin tumor having the appearance of dark purple blotches; [0023] Skin ulcers that resemble a diabetic or venous stasis ulcer; and [0024] Slow healing wounds that often become chronic and are resistant to current modes of treatment.

Applicant's method and apparatus provides to health care practitioners an effective wound care product that has no side effects (except the possibility of a transient local allergic reaction due to added medicaments of choice) or more importantly, unwanted drug interactions.

If an individual has to stop a treatment because of a drug interaction, or for any other reason, it is now widely accepted that the hiatus in treatment may increase the chance of developing subsequent drug resistance to the HIV virus with subsequent development of Aids when they restart their drug cocktails. Applicant's wound care dressing and method using same are beneficial to the long term care of those infected with HIV and Aids.

Applicant's invention includes a nonwoven blanket formed from one or more saccharides in combination with one or more medicaments disposed in and/or on that nonwoven blanket, and a method using Applicant's nonwoven blanket composition. In certain embodiments, Applicant's nonwoven blanket composition, comprising one or more saccharides and one or more medicaments, comprises a wound dressing.

Applicant's nonwoven wound dressings comprise sheet or web structures held together by entangling fibers or filaments. These nonwoven dressings are flat, porous sheets that are made directly from separate fibers. Applicant's nonwoven dressings are not made by weaving or knitting and do not require converting the fibers to yarn.

In certain embodiments, Applicant's nonwoven wound dressing is formed using a "melt blowing" process. As those skilled in the art will appreciate, melt blowing has traditionally been used to produce fibrous webs or articles directly from polymers or resins using high-velocity air or another appropriate force to attenuate the filaments. Applicant has modified this traditional process to use one or more molten saccharides.

Applicant has found that using his melt blowing process he is able to form microfibers rather than fibers the size of normal textile fibers. Using this melt blowing technique, Applicant is able to form a nonwoven wound dressing comprising microfibers generally having diameters in the range of 2 to 4 microns In certain embodiments, Applicant forms his nonwoven wound dressing using a melt blowing process to produce microfibers having diameters in the range from about 0.1 microns to about 15.microns.

Figure 1:
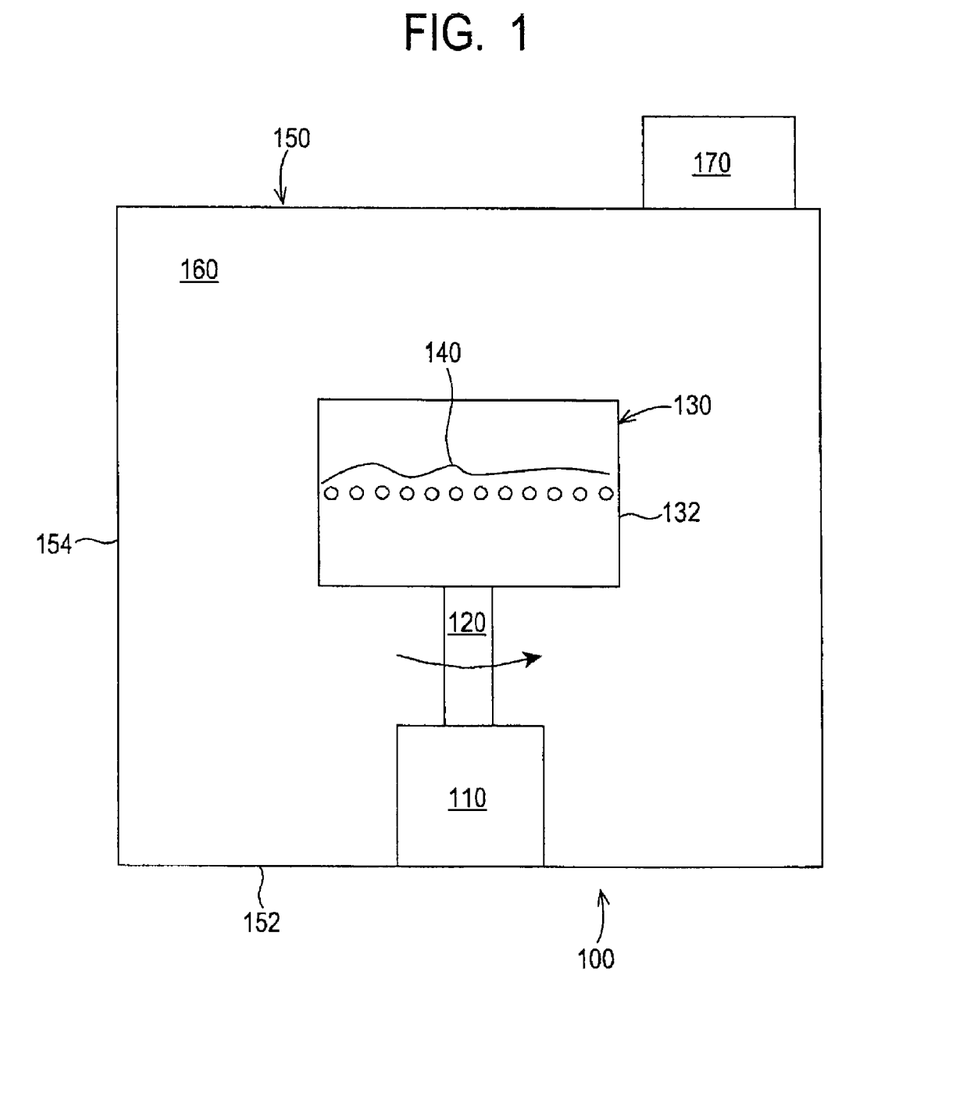
FIG. 1 is a cross-sectional view of Applicant's apparatus used in certain embodiments to form his nonwoven blanket comprising a plurality of fibers formed from a saccharide.

In other embodiments and referring now to FIG. 1, Applicant utilizes an apparatus 100 to form his nonwoven blanket compositions. Apparatus 100 comprises motor 110, external shaft 120, spinerette 130, and enclosure 150. Motor 110 rotates external shaft 120 which in turn rotates spinerette 130. In certain embodiments, enclosure 150 includes floor 152 and bowl-shaped structure 154, wherein structure 154 is releaseably attached to floor 152.

Spinerette 130 is disposed within enclosed space 160 which is defined by enclosure 150. In the illustrated embodiment of FIG. 1, motor 110 is also disposed within enclosure 150. In other embodiments, motor 110 is disposed external to enclosure 150 with shaft 120 disposed through an aperture formed enclosure 150.

Reservoir 160 is maintained at a first temperature. In certain embodiments, that first temperature is room temperature. In other embodiments, apparatus 100 further includes a temperature adjustment device 170 interconnected to structure 150. In certain embodiments, temperature adjustment device 170 comprises a heating device capable of maintaining the first temperature of enclosed space 160 above room temperature. In certain embodiments, temperature adjustment device 170 exchanges heated air with the extant air within enclosure 150.

In certain embodiments, temperature adjustment device 170 comprises a cooling device capable of maintaining the first temperature of space 160 below room temperature. In certain embodiments, temperature adjustment device 170 exchanges cooled air with the extant air within enclosure 150.

Figure 2:
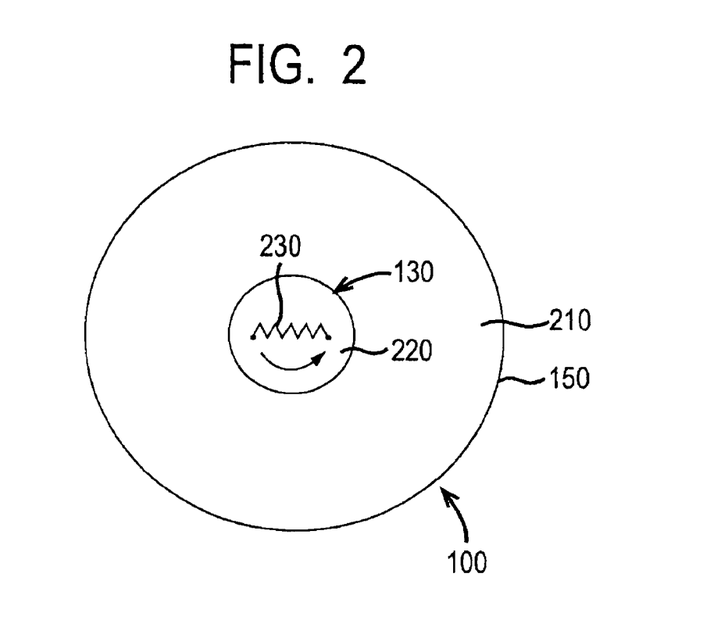
FIG. 2 is a top view of the apparatus of FIG. 1.

Referring now to FIGS. 1 and 2, spinerette 130 includes continuous wall 132 which defines cavity 220, where wall 132 is formed to include a plurality of holes 140. Heating mechanism 230 is disposed within cavity 220. In operation, one or more saccharides are placed into cavity 220 and heated to a second temperature, wherein that second temperature is greater than the melting point(s) of those one or more saccharides. The one or more saccharides are heated until molten. Motor 110 is then operated to rotate spinerette 130.

Figure 9:
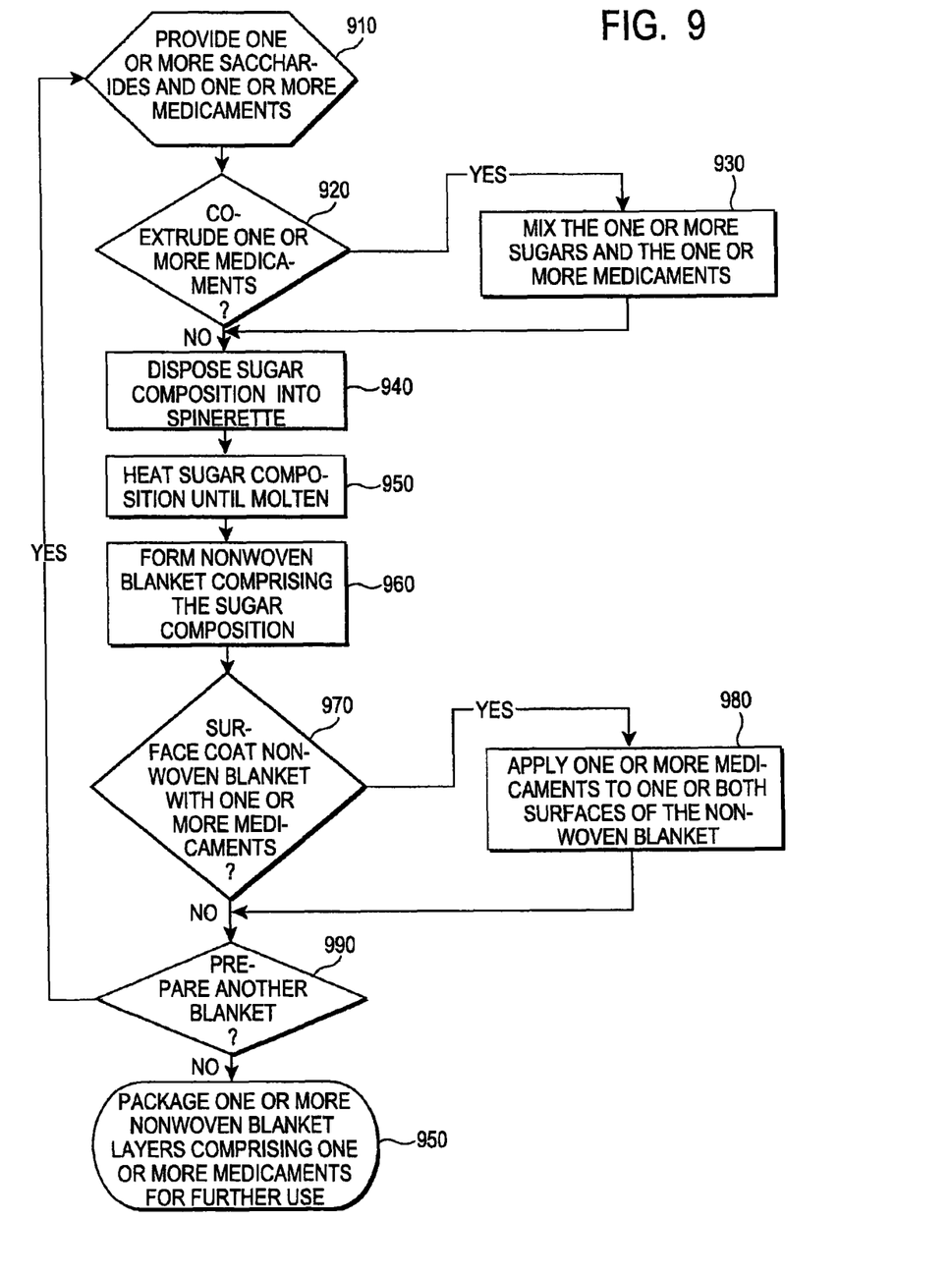
FIG. 9 is a flow chart summarizing Applicant's method to form his wound care dressing.

Referring now to FIG. 9, in step 910 Applicant's method provides one or more saccharides. By "saccharide," Applicant means (i) a mono-saccharide including fructose, glucose, xylose, and the like; (ii) a di-saccharide including sucrose, maltose, cellobiose, lactose, trehalose, and the like; and (iii) polyols comprising (N) carbons and (N) hydroxy groups, wherein (N) is greater than or equal to 4 and less than or equal to 12, such as for example, erythritol, xylitol, mannitol, sorbital, maltitol, isomalt, and lactitol. Table 1 summarizes certain physical properties of these polyols.

TABLE 1

|  | Erythritol | Xylitol | Mannitol | Sorbitol | Maltitol | Isomalt | Lactitol |
|---|---|---|---|---|---|---|---|
| Carbon n° | 4 | 5 | 6 | 6 | 12 | 12 | 12 |
| Molecular Weight | 122 | 152 | 182 | 182 | 344 | 344 | 344 |
| Melting Point (° C.) | 121 | 94 | 165 | 97 | 150 | 145-150 | 122 |
| Glass Transition Temp (° C.) | −42 | −22 | −39 | −5 | 47 | 34 | 33 |
| Heat of Solution (kcal/kg) | −43 | −36.5 | −28.5 | −26 | −18.9 | −9.4 | −13.9 |
| Heat Stability (° C.) | >160 | >160 | >160 | >160 | >160 | >160 | >160 |
| Acid Stability pH | 2-10 | 2-10 | 2-10 | 2-10 | 2-10 | 2-10 | >3 |
| Solubility ww % (25° C.) | 36 | 66 | 18 | 72 | 60 | 28 | 58 |
| Hygroscopicity | Very Low | Low | Very Low | High | Low | Low | Medium |

Figure 4:
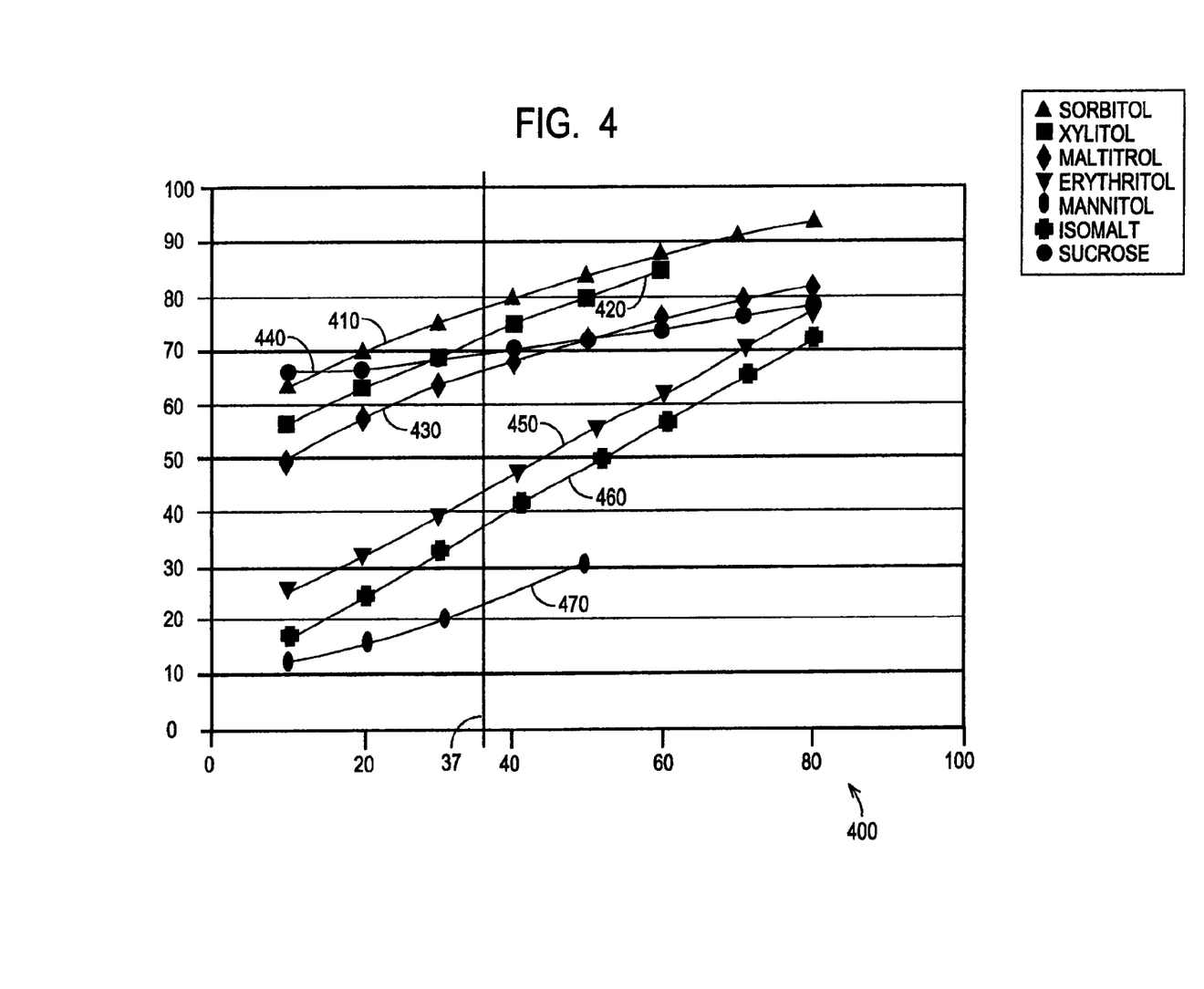
FIG. 4 is a graph depicting the water solubilities of a plurality of polyols used to form Applicant's nonwoven wound care dressing.

Referring now to FIG. 4, graph 400 depicts the solubilities of various polyols in water as a function of temperature. Applicant has discovered that the rate of dissolution of his nonwoven blanket formed from individual saccharide fibers varies proportionately with the water solubility of the constituent saccharide. As the solubility of the saccharide molecule increases, the rate of dissolution of a nonwoven blanket formed from that saccharide also increases.

At about 37.degree. C., i.e. body temperature, the solubility of sucrose is about 78 grams per 100 grams of water. On the other hand, at about 37.degree. C. the solubility of mannitol is only about 23 grams per 100 grams of water. Applicant has found that a nonwoven blanket comprising sucrose dissolves about 3 to 4 times faster in water than does a comparable, i.e. size, shape, and density, nonwoven blanket comprising mannitol.

Referring again to FIG. 9, in step 910 Applicant's method further provides one or more medicaments. In certain embodiments, those one or more medicaments are selected from the group comprising, Dry Powder Betadine sold in commerce by Seton Healthcare; Betadine Solution and Ointment sold in commerce by Purdue Frederick; Isodine Gel sold in commerce by Meiji Seika Kaisha, Ltd (Japan); one or more antibiotics including without limitation Penicillins, Tetracyclines, Gentimycin, Silver (ionic or colloidal); and/or one or more antifungal, one or more antibacterial, one or more antiviral, and/or one or more antiprotozonal medicaments, and the like.

In certain embodiments, step 910 further comprises selecting one or more additives, including but not limited to, one or more anesthetics, such as for example lidocaine, procaine, benzocaine, cocaine, and the like. In certain embodiments, the medicaments/additives of step 910 further comprise, for example and without limitation, various naturally-occurring substances, such as one or more alkaloids and/or alkaloid derivatives. In still other embodiments, the medicaments/additives of step 910 further comprise, for example and without limitation, naturally-occurring substances known in the art to facilitate wound healing, such as and without limitation, coralline algae including geniculate coralline algae and non-geniculate coralline algae (Division—Rhodopyta, Class—Rhodophyceae, Order—Corallingles); coral calcium-derived compositions, brazlian coral, coral algae (red), and the like.

In step 920, Applicant's method determines whether to add one or more of the medicaments of step 910 to the one or more saccharides of step 910 prior to forming Applicant's nonwoven blanket. If the method elects not to combine one or more saccharides and one or more medicaments prior to forming Applicant's nonwoven blanket, then the method transitions from step 920 to step 940. Alternatively, if Applicant's method elects to add one or more of the medicaments of step 910 to the one or more saccharides of step 910 prior to forming Applicant's nonwoven blanket, then the method transitions from step 920 to step 930 wherein the method combines those selected one or more medicaments and the one or more saccharides. Applicant's method transitions from step 930 to step 940 wherein the method disposes the saccharide-based composition of step 910 or step 930 in an apparatus, such as for example apparatus 100 (FIGS. 1, 2, 3), capable of forming a nonwoven blanket from that saccharide-based composition.

In step 950, Applicant's method heats the saccharide based composition to a second temperature, wherein that second temperature is greater than the melting point of each of the saccharides used. Table 1, above, recites, inter alia, the melting points for a variety of saccharides/polyols.

Figure 3:
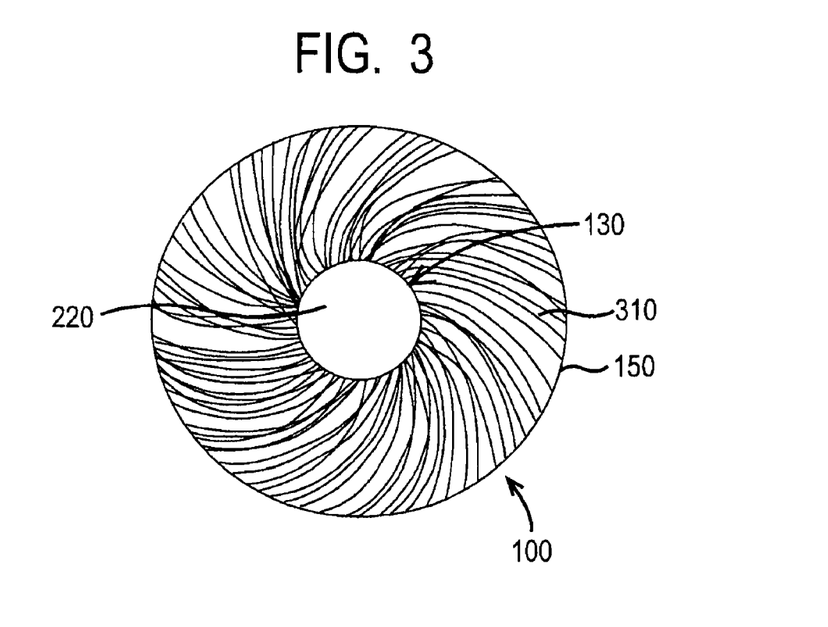
FIG. 3 is a top view of the apparatus of FIG. 1 showing a plurality of fibers disposed in the reservoir portion of the apparatus of FIG. 1, wherein each of the plurality of fibers is formed from a saccharide.

In step 960, Applicant's method forms a nonwoven blanket from the saccharide-based composition of step 910 or step 930. Referring now to FIGS. 1, 2, and 3, as spinerette 130 rotates, the molten saccharide(s) are extruded by a centrifugal force outwardly from spinerette 130 through the plurality of holes 140 into reservoir 160. The temperature of reservoir 160 is maintained at a first temperature, wherein that first temperature is less than the melting point(s) of the one or more saccharides. In certain embodiments, step 960 further includes adjusting the first temperature of space 160 using temperature adjustment device 170.

As the streams of molten saccharide(s) exit plurality of holes 140, those molten streams are cooled by the air of reservoir 160, and form a plurality of individual saccharide fibers 310 disposed within enclosure 150. The plurality of saccharide fibers 310 are removed from enclosure 150 and are used as Applicant's nonwoven blanket.

In step 970, Applicant's method elects whether to dispose one or more of the medicaments of step 910 onto one or both of the surfaces of the nonwoven blanket of step 960. If the method elects not to dispose one or more medicaments onto one or more of the surfaces of the nonwoven blanket of step 960, then the method transitions from step 970 to step 990.

The following examples are presented to further illustrate to persons skilled in the art how to make and use the invention. These examples are not intended as a limitation, however, upon the scope of the invention, which is defined only by the appended claims.

Example I

Applicant used a Paragon International apparatus, Model—Serial #2-304, 120 Volts at 60 Hertz, drawing 11.6 Amps, to produce a nonwoven "floss" to form his nonwoven blanket. After turning motor switch on, the spinning head 130 (FIG. 1) was filled with about 250 ml of sucrose. The HEAT switch was then placed in the "on" position, and the HEAT CONTROL knob was placed in the START/CLEAN position.

Once the floss began to form, HEAT CONTROL knob was placed in the OPERATING RANGE. The production of floss was carefully monitored, and if liquid or crystallized sucrose was emitted from the head, then the HEAT CONTROL knob was adjusted to a lower setting.

When production of the floss slowed, additional sucrose was added without adjusting the HEAT CONTROL knob. After forming the desired quantity of floss, the HEAT switch and HEAT CONTROL knob were placed in the off positions.

When the plurality of saccharide fibers formed in reservoir 160 (FIG. 1) reached the desired thickness, that plurality of saccharide fibers were removed using a wooden spatula. That plurality of saccharide fibers were then placed on wax paper and laid out in a rectangular "swath".

Dry powdered Povidone-Iodine was selected as medicament of choice for this particular embodiment of Applicant's wound care dressing, and about 33 grams of the Povidone-Iodine was substantially uniformly deposited over the top surface of saccharide swath using a stainless steel sifter. This swath was then folded over and a second amount of Dry Povidone Iodine was applied as described above. The Povidone-Iodine deposition and folding process was repeated a total of three times to form a nonwoven blanket comprising of a plurality of saccharide fibers, and further comprising Povidone-Iodine, where that nonwoven blanket had a length of about 12 cm, a width of about 4 cm. and a thickness of about 0.25 cm. This nonwoven blanket comprised about 1.0 grams of Povidone-Iodine. The nonwoven blanket composition was then cut to form individual wound care dressings comprising a desired size and shape. This resultant wound care dressing were subsequently used to treat actual wounds.

Example II

A rectangular swath comprising a plurality of saccharide fibers was formed as described in Example I, above. Thereafter, about 33 grams of powdered Non-geniculate Coralline Algae was substantially uniformly deposited onto the top surface of the saccharide fiber using a stainless steel sifter. This swatch material was then folded over and a second amount of Non-geniculate Coralline Algae was applied as described above. The Non-geniculate Coralline Algae deposition and folding process was repeated a total of three times to form a nonwoven blanket comprising of a plurality of saccharide fibers, and further comprising Non-geniculate Coralline Algae, where that nonwoven blanket had a length of about 12 cm, a width of about 4 cm. and a thickness of about 0.25 cm. This nonwoven blanket comprised about 1.0 grams of Non-geniculate Coralline Algae. The nonwoven blanket composition was then cut to form individual wound care dressings comprising a desired size and shape. This resultant wound care dressing were subsequently used to treat actual wounds.

Figure 5:
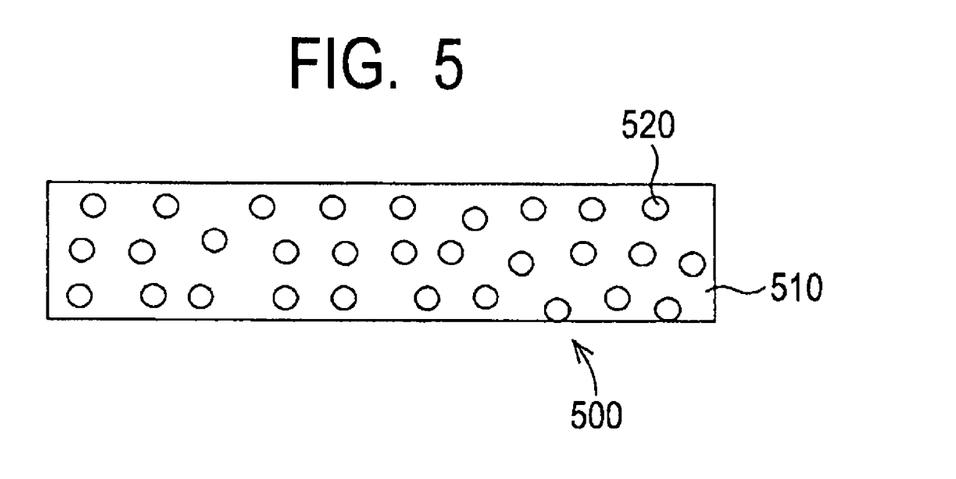
FIG. 5 is a cross-sectional view of a first embodiment of Applicant's wound care dressing comprising a nonwoven blanket formed from a saccharide in combination with one or more medicaments, wherein those one or more medicaments are substantially uniformly dispersed throughout the nonwoven blanket.

Referring to FIG. 5, wound dressing 500 includes a nonwoven blanket 510 formed from one or more saccharides, as described above, in combination with one or more medicament(s) 520. In the illustrated embodiment of FIG. 5, medicament(s) 520 are substantially uniformly dispersed throughout blanket 510. By "substantially uniformly dispersed throughout," Applicant means the concentration, i.e. weight percentage, of medicament(s) 520 varies by plus or minus 10 percent or less throughout nonwoven blanket 510.

For purposes of illustration, FIG. 5 shows those medicaments having a size such that those medicaments can be readily observed. In actual implementation, and as those skilled in the art will appreciate, the plurality of molecules comprising medicament(s) 520 cannot be individually visualized using even traditional magnified viewing devices, i.e. optical microscopes. In certain embodiments, the uniform distribution of medicament(s) 520 throughout nonwoven blanket 510 is achieved by admixing the medicament(s) and the saccharide(s) in step 930 prior to forming the nonwoven blanket in step 960.

Alternatively, if the method elects to dispose one or more medicaments onto one or more of the surfaces of the nonwoven blanket of step 960, then the method transitions from step 970 to step 980 wherein the method disposes one or more medicaments onto one or both surfaces of the nonwoven blanket of step 960. In certain embodiments, step 980 includes spray coating one or both surfaces of the nonwoven blanket with one or more medicaments of step 960. In certain embodiments, step 980 includes calendaring one or more medicaments onto one or both surfaces of the nonwoven blanket of step 960.

Figure 6:
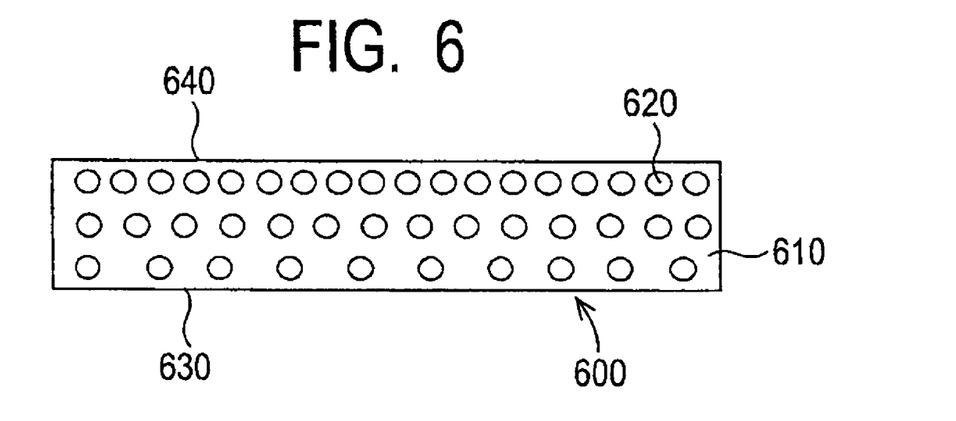
FIG. 6 is a cross-sectional view of a second embodiment of Applicant's wound care dressing comprising a nonwoven blanket formed from a saccharide in combination with one or more medicaments, wherein those one or more medicaments are not uniformly dispersed throughout the nonwoven blanket.

Referring now to FIG. 6, wound dressing 600 includes a nonwoven blanket 610 formed from one or more saccharides, as described above, in combination with medicament(s) 620. Dressing 600 further includes a first surface 630 and a second surface 640. In the illustrated embodiment of FIG. 6, medicament(s) 620 are non-uniformly dispersed throughout blanket 610. By "non-uniformly dispersed throughout," Applicant means the concentration, i.e. weight percentage, of medicament(s) 520 varies by more than plus or minus 10 percent throughout nonwoven blanket 510.

In the illustrated embodiment of FIG. 6, dressing 600 comprises a concentration gradient of medicament(s) 620 from surface 630 to surface 640, wherein the concentration of medicament(s) 620 adjacent surface 640, i.e. the weight percentage of medicament(s) 620 in nonwoven blanket 610 adjacent surface 640, is greater than the concentration of medicament(s) 620 adjacent surface 630. In certain embodiments, the nonuniform distribution of medicament(s) 620 within nonwoven blanket 610 illustrated in FIG. 6 results from applying medicament(s) 620 to one surface of blanket 610. In certain embodiments, the nonuniform distribution of medicament(s) 620 within nonwoven blanket 610 illustrated in FIG. 6 results from first mixing saccharide(s) 610 and medicament(s) 620 in step 930, forming a substantially uniform distribution of medicament(s) 620 throughout blanket 610 in step 960, and then subsequently applying additional medicament(s) 620 to one surface of blanket 610 in step 980.

For purposes of illustration, FIG. 6 shows first medicament(s) 620 having a size such that those medicaments can be readily observed. In actual practice, and as those skilled in the art will appreciate, the plurality of molecules comprising the one or more first medicaments 620 cannot be individually visualized using even traditional magnified viewing devices, i.e. optical microscopes.

Applicant's method transitions from step 980 to step 990 wherein the method determines, after forming the (n)th blanket if the (n+1)th blanket will be prepared. If Applicant's method elects to prepare the (n+1)th blanket, then the method transitions from step 990 to step 910 and continues as described above. Alternatively, if Applicant's method elects not to prepare the (n+1)th blanket, then the method transitions from step 990 to step 995 wherein the method packages the (n) blankets formed for later clinical use.

Referring again to FIG. 5, wound care dressing 500 comprises medicament(s) 520 dispersed throughout saccharide fibers 510. After placement onto a wound, body fluids dissolve the saccharide fibers thereby releasing medicament(s) 520 into the wound. By adjusting the saccharide composition 510, Applicant can adjust the rate at which the medicament(s) 520 are released. Using a saccharide having a greater water solubility, such as for example sorbital, medicament 520 is released more rapidly than using a saccharide having a lesser water solubility, such as mannitol.

Figure 7:
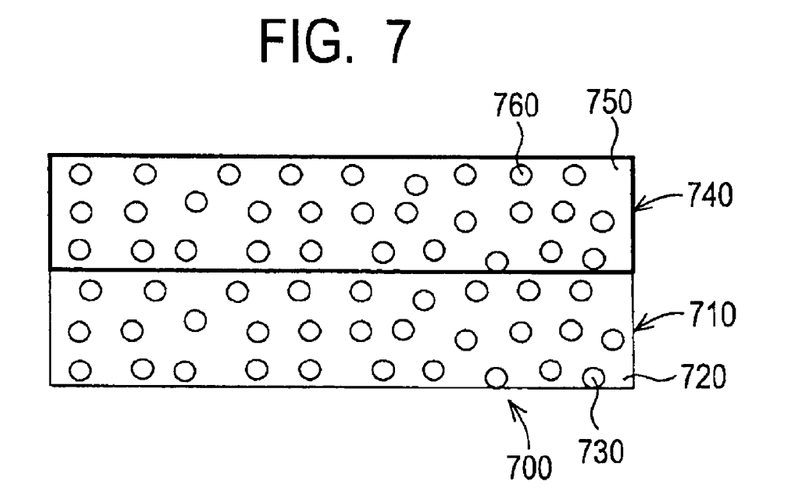
FIG. 7 is a cross-sectional view of a third embodiment of Applicant's wound care dressing comprising two nonwoven blankets formed from two different saccharides and one or two medicaments.

Referring now to FIG. 7, wound care dressing 700 includes first nonwoven blanket 710 and second nonwoven blanket 740. Blanket 710 comprises first saccharide(s) 720 and first medicament(s) 730. In certain embodiments, blanket 710 comprises a substantially uniform distribution of first medicament(s) 730 throughout first saccharide(s) 720. In other embodiments, first blanket 710 comprises a non-uniform distribution of medicament(s) 730 as shown for medicament(s) 620 (FIG. 6) in dressing 600 (FIG. 6).

Blanket 740 comprises second saccharide(s) 750 and second medicament(s) 760. In certain embodiments, blanket 740 comprises a substantially uniform distribution of second medicament(s) 760 throughout second saccharide(s) 750. In other embodiments, second blanket 740 comprises a non-uniform distribution of second medicament(s) 760 as shown for medicament(s) 620 (FIG. 6) in dressing 600 (FIG. 6).

In certain embodiments, the first saccharide(s) 720 differ from the second saccharide(s) 750. In certain of these differing saccharide embodiments, first saccharide 720 has a first rate of dissolution in water and second saccharide 750 has a second rate of dissolution in water. In certain embodiments, the first rate of dissolution is greater than the second rate of dissolution. In other embodiments, the first rate of dissolution is less than the second rate of dissolution.

In certain embodiments, first medicament(s) 730 have a first concentration in first saccharide 720 and second medicaments have a second concentration in second saccharide 750. In certain embodiments, the first concentration is greater than the second concentration. In other embodiments, the first concentration is less than the second concentration.

In certain embodiments, first medicament(s) 730 is the same as second medicament(s) 760. In other embodiments, first medicament(s) 730 differ from second medicament(s) 760.

In embodiments of dressing 700 wherein the first saccharide 720 differs from second saccharide 750, and wherein first saccharide 720 has a first rate of dissolution in water and wherein second saccharide 750 has a second rate of dissolution in water, and wherein the first rate of dissolution is greater than the second rate of dissolution, Applicant's dressing 700 comprises a pulsitile drug delivery system wherein after that dressing is applied to a wound, the first nonwoven blanket 710 dissolves at the first rate of dissolution thereby administering medicament(s) 730 during a first time interval, and 5 the second nonwoven blanket 740 dissolves at the second rate of dissolution thereby administering the medicament(s) 760 over a second time interval, wherein the first time interval precedes, in whole or in part, the second time interval.

In embodiments wherein medicament(s) 730 and 760 are the same, then dressing 700 provides a pulsitile drug delivery system that provides a first dose of the medicament 10 at the first time and a follow-on second dose of the medicament at the second time. In embodiments wherein medicament(s) 730 and 760 differ, then dressing 700 provides a pulsitile drug delivery system that provides a dose of medicament(s) 730 at the first time and then a dose of the medicament(s) 760 at the second time.

Figure 8:
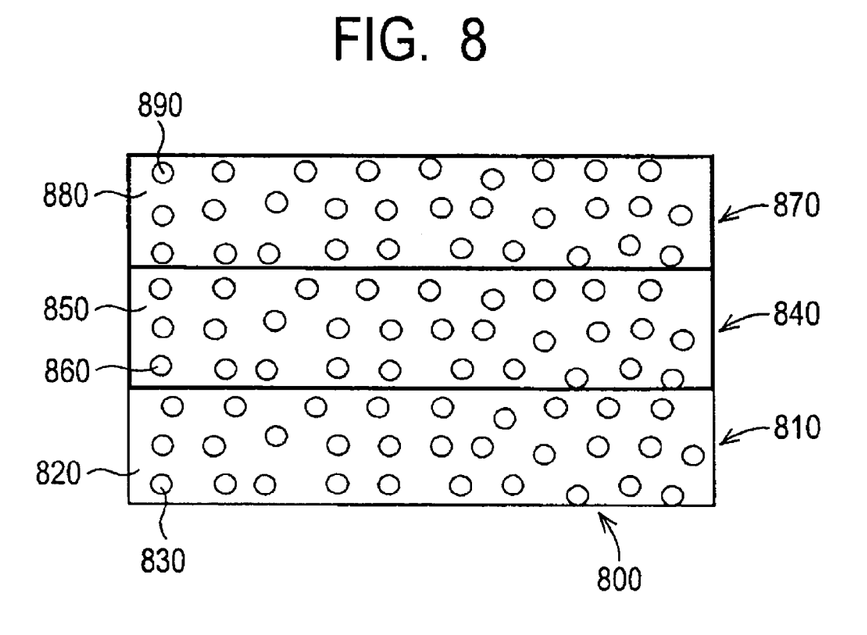
FIG. 8 is a cross-sectional view of a fourth embodiment of Applicant's wound care dressing comprising three nonwoven blankets formed from three different saccharides and one, or two, or three medicaments.

Referring now to FIG. 8, wound care dressing 800 includes first nonwoven 1 5 blanket 710, second nonwoven blanket 840, and third nonwoven blanket 870. Blanket 810 comprises first saccharide(s) 820 and first medicament(s) 830. In certain embodiments, blanket 810 comprises a substantially uniform distribution of first medicament(s) 830 throughout first saccharide(s) 820. In other embodiments, first blanket 810 comprises a non-uniform distribution of medicament(s) 830 as shown for 20 medicament(s) 620 (FIG. 6) in dressing 600 (FIG. 6).

Blanket 840 comprises second saccharide(s) 850 and second medicament(s) 860.

In certain embodiments, blanket 840 comprises a substantially uniform distribution of second medicament(s) 860 throughout second saccharide(s) 850. In other embodiments, second blanket 840 comprises a non-uniform distribution of second medicament(s) 860 as shown for medicament(s) 620 (FIG. 6) in dressing 600 (FIG. 6).

Blanket 870 comprises third saccharide(s) 880 and third medicament(s) 890. In certain embodiments, blanket 870 comprises a substantially uniform distribution of third medicament(s) 890 throughout third saccharide(s) 880. In other embodiments, third blanket 870 comprises a non-uniform distribution of third medicament(s) 890 as shown for medicament(s) 620 (FIG. 6) in dressing 600 (FIG. 6).

In certain embodiments, the first saccharide(s) 820 differs from both the second saccharide(s) 850 and from third saccharide(s) 880. In certain of these differing saccharide embodiments, first saccharide 820 has a first rate of dissolution in water, and second saccharide 850 has a second rate of dissolution in water, and third saccharide 880 has a third rate of dissolution in water. In certain embodiments, the first rate of dissolution is greater than both the second rate of dissolution and the third rate of dissolution. In certain embodiments, the second rate of dissolution is greater than the third rate of dissolution.

In certain embodiments, first medicament(s) 830 have a first concentration in first saccharide 820, and second medicaments 860 have a second concentration in second saccharide 850, and third medicament 890 has a third concentration in third saccharide 880. In certain embodiments, the first concentration, second concentration, and third concentration are substantially the same. In other embodiments, the first concentration and/or second concentration and/or third concentration, differ.

In embodiments of dressing 800 wherein the first saccharide 820, second saccharide 850, and third saccharide 880 differ, and wherein first saccharide 820 has a first rate of dissolution, and second saccharide 850 has a second rate of dissolution, and third saccharide 880 has a third rate of dissolution, and wherein the first rate of dissolution is greater than the second rate of dissolution and the second rate of dissolution is greater than the third rate of dissolution, Applicant's dressing 800 comprises a pulsitile drug delivery system wherein after that dressing is applied to a wound, the first nonwoven blanket 810 dissolves at the first rate of dissolution thereby releasing the first medicament(s) 830 at a first time, and the second nonwoven blanket 840 dissolves at the second rate of dissolution thereby releasing the second medicament(s) 830 at a second time, and the third nonwoven blanket 870 dissolves at the third rate of dissolution thereby releasing the third medicament(s) 830 at a third time.

In embodiments wherein medicament(s) 830, 860, and 890, are the same, then dressing 800 provides a pulsitile drug delivery system that provides a first dose of the medicament at the first time, and a follow-on second dose of the medicament at the second time, and a follow-on third dose at the third time. In embodiments wherein medicament(s) 830, 860, and 890 differ, then dressing 800 provides a pulsitile drug delivery system that provides a dose of the first medicament(s) 830 at the first time and a dose of the second medicament(s) 860 at the second time and a dose of the third medicament(s) 890 at the third time.

Applicant's wound care dressings, such as for example dressing 500, 600, 700, and/or 800, may be used to treat traumatic ulcers, ischaemic ulcers, post-burn ulcers, diabetic ulcers, venous stasis, arteriosclerotic, decubiti/pressure/bed sores, lacerations, burns, plastic surgery, wound dihiscences, amputations, avulsions, abrasions, abscesses, dry sockets (Dental), and skin wounds of all types (Human and Veterinary). Applicant's nonwoven blanket may also be used solely as a pulsitile drug delivery system for various medicaments that require various adsorption schedules.

Applicant's wound care dressings, such as or example dressing 500, 600, 700, and/or 800, may be applied to various open wounds and burns as a matrix of "gauze-like" material that looks and is manipulated like regular cotton gauze bandaging material. Therefore, Applicant's wound care dressings, such as for example dressing 500, 600, 700, and/or 800, may be applied in various sizes ranging from: 2.times.2's to 12.times.12's; rolls, pads; strips, bandages, tapes, and whatever else conventional gauze or dressing material may be used for in a hospital, outpatient- or home setting.

In certain embodiments, the saccharide content comprises the majority of Applicant's nonwoven wound care dressing ranges from about 50 to about 99 weight percent of the overall weight of the resulting "fabric" or loose "ball." In other embodiments, Applicant's wound care dressing comprises between about 1 to about 49 weight percent of a composition further comprising a collagen-derived scaffolding matrix, and/or a hydrogel-cell matrix, and/or other "back bone" scaffolding matrices, wherein Applicant's nonwoven wound care dressing facilitates the delivery of one or more of the medicaments and/or additives described above in conjunction with step 910 (FIG. 9).

In certain embodiments, Applicant's wound care dressings, such as for example dressing 500, 600, 700, and/or 800, comprise a nonwoven mesh that is about 10 mil thick for application to an incision strip closure (e.g. a "steri-strip") with placement in the center over the suture line. In other embodiments, Applicant's wound care dressings, such as for example dressing 500, 600, 700, and/or 800, comprises a very loose nonwoven packing material, like cotton candy at the fair, for use in a large defect like a decubitus ulcer and anything in-between. Applicant's wound care dressing may be in the form of a tightly compressed "tape" of nonwoven fibers that is packed into a wound while being fed from a roll.

In certain embodiments, Applicant's wound care dressings, such as for example dressing 500, 600, 700, and/or 800, further includes one or more ingredients for performing specific desired additional functions; for example, super absorbents, tackifiers, fillers, bactericides, cleansers, disinfectants, coagulants, analgesics, medicaments like ionic silver, or other bioactive agents.

Applicant's wound care dressings, such as for example dressing 500, 600, 700, and/or 800, may be changed once, twice, three times daily, or per health care orders, depending on the type of wound and if there are large amounts of exudates, infection (gram+ or gram-bacteria, pseudomonas. etc.), and the like.

The benefits of using Applicant's wound care dressings, such as for example dressing 500, 600, 700, and/or 800, include ease of application. The application of a wrap, sheet, roll, or strip of Applicant's wound care dressings, such as for example dressing 500, 600, 700, and/or 800, that is primarily made of spun or nonwoven saccharide fibers that are able to wrap around and lay on structural curves present externally (face) as well as internally (blood vessels). In addition, Applicant's wound care dressings, such as for example dressing 500, 600, 700, and/or 800, can be handled manually using fingertips without getting wet or without falling off if not secured. Moreover, Applicant's wound care dressings, such as for example dressing 500, 600, 700, and/or 800, may be used without requiring a spoon or tongue depressor to scoop and/or apply. Furthermore, Applicant's wound care dressings, such as for example dressing 500, 600, 700, and/or 800, can be applied with using a backing material that is adhesive to the skin.

Each of these applications comprises a superior method with respect to the prior art method of application that requires the paste material be manually spread onto gauze, held against the wound if gravity is not able to hold it in place, and taped with an occlusive dressing or Kerlex wrap—which is often, depending on the site of the wound, a four-handed procedure.

In addition, it has long been documented that simple saccharide and povidone-iodine mixtures are chemically unstable, physically not homogeneous and have low spread ability. Even when improved vehicles are used, they are difficult to use in a clinical, nursing or home care setting.

As those skilled in the art will appreciate, the prior art paste is granular which can severely irritate a wound where any movement or surface pressure is involved. In marked contrast, direct application to a wound of Applicant's wound care dressings, such as for example dressing 500, 600, 700, and/or 800, will not have the affect of sandpaper and will be easier to tolerate.

The prior art paste exhibits a tendency to burn or "smart" in superficial wounds, most likely due to the liquid povidone-iodine solutions. Applicant's wound care dressings, such as for example dressing 500, 600, 700, and/or 800, comprise dry ingredients which are less likely to cause the reaction a wet liquid that saturates an area can have.

Using Applicant's wound care dressings, such as for example dressing 500, 600, 700, and/or 800, offers a comparatively low cost, far superior alternative to prior art pastes with respect to application, storage, transportation, shelf life, patient acceptability, and patient comfort.

Applicant's wound care dressing 500, 600, 700, and/or 800, may be used in combination with:

Hydrocolloid Dressings—Hydrocolloid dressings are made up of a matrix of cellulose and other gel-forming agents such as gelatin and pectin. It is an occlusive dressing that helps maintain a moist wound healing environment. It also promotes autolysis and granulation. The dressings can be manufactured "thin" or "thick" with film or foam top.

Foam Dressings—Highly absorbent dressings generally made from hydrophilic polyurethane foam. The dressing can be supplied with adhesive border around the foam, if desired. Foam dressings require less frequent changes because they absorb and hold a high amount of exudate.

Thin Film Dressings—Transparent thin film dressings are semi-permeable membranes that are waterproof, yet allow oxygen and water vapor to pass through. The dressings help fight bacterial contamination, and help maintain a moist wound environment. There are several new films on the market that offer very high Moisture Vapor Transmission Rates (MVTR). These films have been used traditional in the IV site market and not for chronic wounds. Thin film dressings are often used as a cover for a primary dressing. Thin film dressings will play a major role in Applicant's method for skin transplantation of cells (e.g. epidermal) using a saccharide nonwoven blanket as a type of "nursery" for cells to grow and multiply. The high MVTR's of a thin film dressing offers apparent superior protective qualities necessary for use during this sensitive period of growth over a traditional (cotton) gauze sponge. As those skilled in the art will appreciate, other present and future coverings offer additional benefit over thin films (better regulation of fluids and vapors coming in and out), and they are included within the scope of Applicant's invention.

Composite Dressings—Composite dressings are those that combine physically distinct components into a single dressing. For instance, a dressing may contain an absorbent center pad that is island placed on a moisture barrier film backing. Composite dressings can be made of films, foams, nonwovens, and other wound care materials.

Bordered Gauze Dressings—These dressings usually consist of an absorbent pad with a non-stick contact layer that is surrounded by an adhesive border. Bordered gauze dressings are often used as secondary dressings to hold a primary dressing in place.

Wound Closure Strips—Wound closure strips are a primary wound dressing that are used to help close a surgical wound either with or without sutures. They consist of strips of nonwoven material that may be reinforced for added strength. These strips are supplied on a card for ease of dispensing.

In certain embodiments, Applicant's nonwoven wound care dressing is used in combination with a collagen-derived scaffolding matrix, wherein that matrix is implanted to provide subsequent epithelization of a skin defect following a burn injury or traumatic injury to the surface epithelium. Use of such a collagen scaffolding matrix facilitates growth of tissue precursor cells and formation of new tissue. Use of Applicants' nonwoven wound care dressing in combination with a collagen-derived scaffolding matrix is not limited to external surfaces of skin, organs, bone, and/or cartilage, but also to use on internal surface such as the interior surface of a blood vessel.

In certain embodiments, Applicant's nonwoven wound care dressing is used in combination with a liquid hydrogel-cell composition to form a matrix that facilitates precursor cells to grow and generate new tissue. Use of Applicant's nonwoven wound care dressing in combination with a liquid hydrogel-cell matrix is not limited to external surfaces of skin, organs, bone, and/or cartilage, but also to use on internal surface such as the interior surface of a blood vessel.

In certain embodiments, Applicant's nonwoven wound care dressing is used in combination with other "back-bone"

matrices, including without limitation cotton gauze sponges, rolls, bandages, tapes, and the like, to form a matrix that facilitates precursor cells to grow and generate new tissue. Use of Applicant's nonwoven wound care dressing in combination with a back-bone matrix is not limited to external surfaces of skin, organs, bone, and/or cartilage, but also to use on internal surface such as the interior surface of a blood vessel.

In certain embodiments, Applicant's nonwoven wound care dressing is used in combination with a nascent skin graft formed by application of precursor cells onto a wound area. The preparation and use of such a nascent skin graft is described in U.S. Provisional Patent Application having Ser. No. 60/705,906, and entitled Apparatus and Method to Treat a Burn Injury. That U.S. Provisional Patent Application having Ser. No. 60/705,906 is hereby incorporated herein by reference. In certain embodiments, such precursor cells are sprayed onto the wound area. In certain of these spray embodiments, a mechanical apparatus utilizing one or more pressurized gases is used. In other of these spray embodiments, the precursor cells are manually sprayed onto the would area using a syringe. In certain embodiments, such a sprayed-in-place nascent skin graft is formed on top of, in the middle of, and/or below, Applicant's nonwoven wound care dressing.

Applicant's invention comprises a method to treat a patient having a wound, and in need thereof, with a therapeutically effective amount of a medicament. The method provides Applicant's wound care dressing comprising a nonwoven blanket comprising a medicament and a plurality of fibers, wherein that plurality of fibers are formed from a saccharide. The method disposes the wound care dressing over the wound. As those skilled in the art will appreciate, a wound area exudes, inter alia, aqueous-based bodily fluids. Those aqueous-based bodily fluids dissolve the plurality of saccharide fibers thereby releasing the medicament into the wound.

Applicant's invention further comprises a pulsitile method to treat a patient having a wound, and in need thereof, with a therapeutically effective amount of a first medicament, and with a therapeutically effective amount of a second medicament. In this embodiment, Applicant's method provides a wound care dressing comprising a first nonwoven blanket comprising a first medicament and a first plurality of fibers, wherein that first plurality of fibers are formed from a first saccharide comprising a first rate of dissolution in water, and a second nonwoven blanket comprising a second medicament and a second plurality of fibers, wherein that second plurality of fibers are formed from a second saccharide comprising a second rate of dissolution in water, wherein the first saccharide differs from the second saccharide, and wherein the first rate of dissolution in water is greater than the second rate of dissolution in water, and wherein the first medicament differs from the second medicament.

Applicant's method disposes the pulsitile wound care dressing over the wound. The bodily fluids associated with the wound dissolve during a first time interval the first nonwoven blanket, thereby applying the first medicament to the wound area during that first time interval. The method then dissolves during a second time interval the second nonwoven blanket, thereby applying the second medicament to the wound area during that second time interval.

The following examples are presented to further illustrate to persons skilled in the art how to make and use the invention. These examples are not intended as a limitation, however, upon the scope of the invention, which is defined only by the appended claims.

Example III

A fifty-six year old female patient presented with Post-Surgical Wound Dihiscience after Breast Reduction. The patient had experienced six weeks duration without improvement.

On DAY 1, and prior to first application of Applicant's wound dressing open incisions were draining with pus, where those incisions were odorous and tender to the touch. The application of any sort of paste or liquid was not feasible due to the location of the incisions on rounded breast areas. Visible areas of erythema and swelling were significant. The Patient had a low grade fever.

The affected area was gently cleansed with warm water, and the surrounding area was towel dried afterwards avoiding further tissue maceration from excess moisture. The infected incisions were covered with a ⅛ inch thick wound care dressing prepared as described in Example I herein, in combination with an occlusive dressing, wherein the wound care dressing comprised a nonwoven blanket formed from fibers consisting of sucrose, and wherein Applicant's wound care dressing further comprised dry povidone-iodine USP powder.

On DAY 2, areas of erythema (redness) and edema (swelling) were greatly reduced. In addition, the open incisional areas were reduced in size by about 20 percent. Applicant noted a large amount of yellowish drainage present with each dressing change. The Patient reported decreased pain and discomfort. In addition the Patient's fever was reduced, with the Patient's temperature measured to be about near normal. The wound care dressing changes continued to be TID.

On DAY 4, areas of erythema (redness) and edema (swelling) continued to decrease, and the open incisional areas were reduced in size by about 50 percent. The treating physician noted that the large amounts of yellowish drainage present early on were now clear and serous with each dressing change. Applicant further observed that the affected area was filling in nicely with granulation tissue. In addition, the Patient reported no pain and only a slight discomfort. Moreover, Patient was afebrile for first time in 5 weeks. Dressing changes were being done twice a day.

On DAY 7, areas of erythema (redness) and edema (swelling) were gone, and areas surrounding the closing incisions appeared normal. The treating physician noted that the open incisional areas were reduced in size by about 80 percent. In addition, the incisions appeared to be "pulling" together. Granulation tissue was still forming nicely and filling in the defect. The Patient reported no pain and was afebrile. On DAY 14, the incisions had approximated and appeared to be closed by primary intention.

Example IV

A forty-four year old male presented with Status Post Skin Evulsion on his forehead. On DAY 1, and prior to first application of Applicant's wound care dressing, acute trauma secondary to skin evulsion caused by a shower faucet pipe was observed. The treating physician concluded that Applicant's wound care dressing would be easier to use because of the location and the curvature of the head.

The affected area was gently cleansed with warm water, and the surrounding area completely towel dried. The wound area was covered with a ⅛ inch thick wound care dressing formed as described in Example II herein, in combination with an occlusive dressing, wherein the wound care dressing comprised a nonwoven blanket formed from fibers consisting of sucrose, and wherein Applicant's wound care dressing further comprised a dry pulverized coralline algae.

On DAY 2, areas of erythema (redness) and edema (swelling) were greatly reduced, and the avulsed area visually appeared to be reduced in size by about 10 percent. In addition, the wound appeared clean and not infected. The Patient was afebrile. Moreover, granulation tissue was filling in from the sides, and bleeding had stopped. The wound care dressing changes continued to be TID.

On DAY 4, the swelling was gone and defect was clean. In addition, the avulsed area continued to fill in with granulation tissue, from the bottom up and from the sides in. The wound care dressings were changed twice a day.

On DAY 7, the avulsed area had completely filled in. The skin defect was slightly lighter in color than normal skin, with no apparent signs of abnormal scar tissue forming.

While the preferred embodiments of the present invention have been illustrated in detail, it should be apparent that modifications and adaptations to those embodiments may occur to one skilled in the art without departing from the scope of the present invention as set forth in the following claims.

I claim:

1. A wound care dressing, comprising:
an overall saccharide fiber weight percentage of 99 weight percent, said wound care dressing further comprising:
a first water soluble nonwoven blanket comprising a first plurality of fibers, wherein said first plurality of fibers are formed from a first water soluble saccharide comprising a first rate of dissolution in water; and
a second water soluble nonwoven blanket comprising a second plurality of fibers, wherein said second plurality of fibers are formed from a second water soluble saccharide comprising a second rate of dissolution in water;
wherein said first saccharide differs from said second saccharide, and wherein said first rate of dissolution in water is greater than said second rate of dissolution in water.

2. The wound care dressing of claim 1, wherein said first saccharide is selected from the group consisting of a mono-saccharide, a di-saccharide, and a polyol comprising (N) carbons and (N) hydroxy groups, wherein (N) is greater than or equal to 4 and less than or equal to 12.

3. The wound care dressing of claim 1, further comprising a first medicament selected from the group consisting of an antifungal medicament, an antibacterial medicament, an antiviral medicament, an antiprotozonal medicament, a coagulant and an anesthetic.

4. The wound care dressing of claim 3, wherein said first medicament is substantially uniformly dispersed throughout said first nonwoven blanket.

5. The wound care dressing of claim 3, wherein said first nonwoven blanket comprises a first surface and an opposing second surface, wherein said first medicament comprises a first weight percentage in said first nonwoven blanket adjacent said first surface and a second weight percentage in said first nonwoven blanket adjacent said second surface, wherein said first weight percentage is greater than said second weight percentage.

6. The wound care dressing of claim 1, wherein said second saccharide is selected from the group consisting of a mono-saccharide, a di-saccharide, and a polyol comprising (N) carbons and (N) hydroxy groups, wherein (N) is greater than or equal to 4 and less than or equal to 12.

7. The wound care dressing of claim 6, further comprising a second medicament selected from the group consisting of an antifungal medicament, an antibacterial medicament, an antiviral medicament, an antiprotozonal medicament, a coagulant, and an anesthetic, wherein said first medicament differs from said second medicament.

8. The wound care dressing of claim 7, wherein said second medicament is substantially uniformly dispersed throughout said second nonwoven blanket.

9. The wound care dressing of claim 7, wherein said second nonwoven blanket comprises a first surface and an opposing second surface, wherein said second medicament comprises a first weight percentage in said second nonwoven blanket adjacent said first surface and a second weight percentage in said second nonwoven blanket adjacent said second surface, wherein said first weight percentage is greater than said second weight percentage.

10. A wound care dressing pulsitile drug delivery system, comprising:
an overall saccharide fiber weight percentage of 99 weight percent, said wound care dressing further comprising:
a first water soluble nonwoven blanket comprising a first medicament and a first plurality of fibers, wherein said first plurality of fibers are formed from a first water soluble saccharide comprising a first rate of dissolution in water; and
a second water soluble nonwoven blanket comprising a second medicament and a second plurality of fibers, wherein said second plurality of fibers are formed from a second water soluble saccharide comprising a second rate of dissolution in water;
wherein said first saccharide differs from said second saccharide, and wherein said first rate of dissolution in water is greater than said second rate of dissolution in water, and wherein said first medicament differs from said second medicament.

11. The wound care dressing pulsitile drug delivery system of claim 10, wherein: said first saccharide is selected from the group consisting a mono-saccharide, a di-saccharide, and a polyol comprising (N) carbons and (N) hydroxy groups, wherein (N) is greater than or equal to 4 and less than or equal to 12; and said second saccharide is selected from the group consisting a mono-saccharide, a di-saccharide, and a polyol comprising (N) carbons and (N) hydroxy groups, wherein (N) is greater than or equal to 4 and less than or equal to 12.

12. The wound care dressing pulsitile drug delivery system of claim 10, wherein said first medicament is selected from the group consisting of an antifungal medicament, an antibacterial medicament, an antiviral medicament, an antiprotozonal medicament, a coagulant and an anesthetic.

13. The wound care dressing pulsitile drug delivery system of claim 12, wherein: said second saccharide is selected from the group consisting a mono-saccharide, a di-saccharide, and a polyol comprising (N) carbons and (N) hydroxy groups, wherein (N) is greater than or equal to 4 and less than or equal to 12; and said second saccharide is selected from the group consisting of a mono-saccharide, a di-saccharide, and a polyol comprising (N) carbons and (N) hydroxy groups, wherein (N) is greater than or equal to 4 and less than or equal to 12.

14. The wound care dressing pulsitile drug delivery system of claim 10, wherein: said second medicament is selected from the group consisting of an antifungal medicament, an antibacterial medicament, an antiviral medicament, an antiprotozonal medicament, a coagulant and an anesthetic; and said second medicament is selected from the group consisting of an antifungal medicament, an antibacterial medicament, an antiviral medicament, an antiprotozonal medicament, and an anesthetic.

* * * * *